United States Patent [19]

Chambers et al.

[11] Patent Number: 5,047,328
[45] Date of Patent: Sep. 10, 1991

[54] METHOD FOR DETERMINATION OF THE TYPE AND SEVERITY OF PERIODONTAL DISEASE STATES

[75] Inventors: Donald A. Chambers, Evanston, Ill.; Thomas E. Schindler, San Diego, Calif.

[73] Assignee: The Board of Trustees of the University of Illinois, Urbana, Ill.

[21] Appl. No.: 262,995

[22] Filed: Oct. 26, 1988

[51] Int. Cl.$^5$ .......................... C12Q 1/52; C12Q 1/48
[52] U.S. Cl. .......................................... 435/16; 435/15
[58] Field of Search ........................ 435/7, 15, 16, 810

[56] References Cited

U.S. PATENT DOCUMENTS 4,801,535  1/1989  Babler et al. ....................... 435/184

FOREIGN PATENT DOCUMENTS

| 0151536 | 8/1985 | European Pat. Off. | |
| 0022698 | 2/1982 | Japan | 435/16 |
| 0024181 | 2/1985 | Japan | 435/16 |
| 0169766 | 9/1985 | Japan | 435/25 |
| 87/00541 | 9/1987 | World Int. Prop. O. | |

OTHER PUBLICATIONS

Chambers, et al., J. Periodon., 55, No. 9, 526–530 (Sep. 1984).
Haffajee, et al., J. Clin. Perio., 10:257–265 (1983).
Kornman, J. Period. Res., 22 (1987).
Lamster, et al., J. Periodontal., 56, 139–147 (1985).
Loe, et al., Acta Odont. Scand., 21:533 (1963).
Mukherjee, et al., J. Dental Research, 62:196, Abstract No. 242 (Mar. 1983).
Ramfjord, J. Periodontal., 30:602 (1967).
Crawford, et al., J. Dental Research, 62:196 Abstract No. 241 (Mar. 1983).
Lamster, et al., J. Clin. Periodontal, 13, 799–804 (1986).
Binder, et al., J. Periodon. Res., 22; 14–19 (1987).
Fiorello, et al., (Abstract 1008) J. Dent. Res., 66, 232 (1987).
Harper, et al, (Abstract 1191) J. Dent. Res., 66, 285 (1987).
Lamster, et al., J. Clin. Periodontol., 12, 153–161 (1985).
Lamster, J. Periodontol. (Supp.), 56, 13–21 (1985).
Lamster, et al., J. Periodontol., 58, 614 (1987).
Lamster, et al., J. Periodontol., 59, 516–523 (Aug. 1988).

*Primary Examiner*—Esther L. Kepplinger
*Assistant Examiner*—Toni R. Scheiner
*Attorney, Agent, or Firm*—Marshall, O'Toole, Gerstein, Murray & Bicknell

[57] ABSTRACT

Disclosed are methods for determining the severity and type of periodontal disease in mammals. The methods include the steps of (1) sampling crevicular fluid for a selected brief period of time, (2) assaying the crevicular fluid sample by colorimetric or other means to determine the total quantity of aspartate aminotransferase present, and (3) correlating the total quantity of aspartate aminotransferase present in the crevicular fluid sample with a standard for the selected sampling period which is indicative of the severity and type of periodontal disease.

7 Claims, 4 Drawing Sheets

FIG. 1a

FIG. 2

METHOD FOR DETERMINATION OF THE TYPE AND SEVERITY OF PERIODONTAL DISEASE STATES

BACKGROUND OF THE INVENTION

The invention relates generally to methods for determining the presence of active periodontal disease in mammals and specifically to those methods for determining the presence of periodontal disease which involve assaying crevicular fluid for the presence of elevated levels of aspartate aminotransferase. More specifically, the invention relates to improvements in such methods which provide for determination of the type and severity of periodontal disease.

Periodontal diseases are inflammatory diseases of microbial etiology affecting the supporting tissues of the teeth. The term "periodontal disease" encompasses two major and distinct subclasses of disease, gingivitis and periodontitis. Gingivitis is characterized by inflammation of the gums without bone loss or loss of connective tissue attachment. Gingivitis is a precondition for, but does not necessarily lead to, periodontitis which is characterized by progressive formation of periodontal pockets between the gum tissue and tooth, resulting from loss of connective tissue attachment and bone loss, eventually leading to tooth loss. Presently available methods of measuring periodontal disease include subjective observational indices such as those of Loe, H. and P. Silness, Acta Odont. Scand. 21:533 (1963) for gingivitis and Ramfjord, S., J. Periodontal. 30:602 (1967) for periodontitis. These indices for periodontitis are based on criteria such as bleeding on gentle probing, pocket depth, attachment loss, and radiographic evidence of bone loss. Unfortunately, these clinical indicators, with the exception of bleeding on probing, are generally acknowledged to be reflective of past disease and prior damage. Of these indicators, only bleeding on probing (bleeding of gum tissue due to probing of the gum line or pocket with a hard instrument, e.g. probe or curet) has been claimed to correlate with active periodontal disease. Nevertheless, bleeding itself is a subjective indicator of disease and the diagnostic value of bleeding on probing has been questioned as such bleeding appears to be associated with a high proportion of false positive indications of periodontal disease. See Haffajee, A.D., S. S. Socransky, and J. M. Goodson, J. Clin. Perio. 10:257-265 (1983).

Other methods have been proposed for the diagnosis of periodontal disease. Because both gingivitis and periodontitis are characterized by accumulation and flow of crevicular fluid (a transudate of serum) at the gingival sulcus and pockets, measurement of the volume of crevicular fluid present at a site has been proposed as a diagnostic for periodontal disease. An instrument known as the Periotron (Harco Electronics Ltd.; Winnipeg, Canada) makes use of this principle by galvanometrically measuring the volume of crevicular fluid absorbed by small strips of porous material known as Periopaper (Harco; Tustin, California) which are inserted into the crevicular space between the tooth and gum.

Still other methods relate to analysis of components of crevicular fluid for the diagnosis of periodontal disease. Kornman, J. Period. Res., 22, (1987) discloses methods correlating the presence of collagenase in crevicular fluid with the severity of periodontal disease. A device (Periocheck, Advanced Clinical Technologies, Inc., Westwood, Mass.) is available which assays for neutral proteases to determine the presence of periodontal disease. The source of both collagenase and neutral proteases has been suggested to be polymorphonuclear leucocytes (PMN) migrating into the crevice. Other components of crevicular fluid such as chondritin-4-sulfate, the presence of which is considered indicative of bone destruction, have been found to differ in crevicular fluid associated with gingivitis and crevicular fluid associated with periodontitis. Prostaglandin $E_2$, a mediator of inflammation, has also been indicated to be associated more closely with periodontitis than with gingivitis.

Of particular interest to the present invention is the disclosure that the presence of elevated levels of the enzyme aspartate aminotransferase (AST) in crevicular fluid is highly correlative of the presence of active periodontal disease. The correlation was first related in two abstracts presented at the American Association for Dental Research Meetings, Cincinnati, Ohio, Mar. 17-20, 1983 (Crawford, J.M., S. Mukherjee, D.A. Chambers, and R. Cohen, Abstract No. 241, and Mukherjee, S., J. Crawford, D.A. Chambers, and R Cohen, Abstract No. 242 both published on or after February 1, 1983) and in an article, Chambers, D.A., J.M. Crawford, S. Mukherjee and R. Cohen, J. Periodon., 55, No. 9, 526-530 (September, 1984). The Crawford et al., abstract discloses a study with dogs in which gingivitis and periodontitis were induced experimentally. Specifically, gingival health was established in five beagles and gingivitis was then allowed to develop for four weeks by introduction of a soft diet and withdrawal of brushing. Periodontitis was then induced by ligation of the dogs' teeth. Crevicular fluid samples were collected at weekly intervals in volumetric capillary tubes after isolation and drying of teeth. The abstract indicates that crevicular fluid obtained during the incidence of experimental periodontitis contained concentrations of AST (3209±1435 SFU/ml) approximately ten-fold higher at their peak than prior to ligation (468±164 SFU/ml) and further that crevicular fluid during the incidence of experimental gingivitis contained approximately ten-fold higher concentrations of AST than in serum (41±4 SFU/ml).

The Chambers et al., J. Periodontal. article describes the dog study in greater detail and notes that the average AST levels in crevicular fluid correlated neither with clinical estimations of attachment levels nor with gingival inflammation. The article did note, however, that the AST peak occurring 2 weeks after ligation of teeth did coincide with the period of high levels of soft tissue destruction and osteoclast activity reported in the beagle dog model and with the period of active bone resorption in ligature-induced periodontitis in the monkey model. The article also disclosed that the level of AST in crevicular fluid did not correlate with enzyme levels in dental plaque, suggesting the absence of bacterial origin for the enzyme.

The Mukherjee Abstract describes measurement of AST levels in human crevicular fluid collected in volumetric capillary tubes from areas diagnosed as having gingivitis or periodontitis according to the periodontal disease index (PDI) of Ramfjord. Disease activity indicated by the presence or absence of bleeding upon probing was also noted. AST concentrations of crevicular fluid collected from areas showing no bleeding on probing=0 SFU/ml (N=4), minimal bleeding=464±113

SFU/ml (N=4) and definite bleeding 595±192 SFU/ml (N=6). The analysis of data sorted according to gingivitis and periodontitis showed 363±182 SFU/ml (N=4) and 424±119 SFU/ml (N=3) respectively. The Abstract notes that the level of AST in crevicular fluid may correlate with the disease activity as determined by bleeding on probing.

While the references fail to demonstrate a specific positive association between elevated AST activity in gingival crevicular fluid and either attachment loss or gingival inflammation, they do indicate that there exists a general association between elevated AST levels in gingival crevicular fluid and periodontal disease activity as determined by bleeding on probing. Chambers, European Patent Application No. 151,536 published August 14, 1985 based on U.S. Pat. application Ser. No. 575,552 filed Jan. 31, 1984, since abandoned and continued as U.S. Ser. No. 06/814,065 filed Dec. 19, 1985, since abandoned, and continued as U.S. Ser. No. 07/096,803 filed Sept. 10, 1987, since abandoned, and continued as U.S. Ser. No. 07/317,138 filed Mar. 1, 1989 the disclosure of which is hereby incorporated by reference, relates to the work embodied in the article and abstracts and the recognition of the general relationship between elevated AST levels and periodontal disease activity. The application claims diagnostic methods based on the recognition that the presence of elevated levels of AST in crevicular fluid is predictive of a high probability of progressive, as opposed to nonprogressive, periodontal disease and corresponding tissue damage.

According to the method of the Chambers patent application, crevicular fluid is collected from the gingival sulcus by means such as a microsyringe, capillary tube or absorbant strip. The volume of material is measured and the concentration of AST in the collected sample of crevicular fluid is determined by either colorimetric or immunological assay. The patent application claims a method for determining the presence of active periodontal disease in mammals comprising assaying crevicular fluid for the presence of elevated levels of aspartate aminotransferase. The application defines elevated levels as being an amount of AST substantially in excess of the level of AST normally found in the blood stream of healthy adults of the species being tested which ranges from about 4 to about 32 milli-International Units/ml (mIU/ml) depending upon the precise testing protocol used.

Since the original reports of work by the Chambers, et al. group on AST, the relationship between other tissue and bacterial enzymes and periodontal diseases has been studied. Lamster, et al., J. Periodontal., 56, 139-147 (1985), disclose studies assessing crevicular fluid volume and activity of the enzymes lactate dehydrogenase (LDH), β-glucuronidase (BG) and arylsulfatase (AS) in crevicular fluid during the development of experimental gingivitis.

LDH is said to be derived primarily from cells in the sulcular epithelium, but that fibroblasts and polymorphonuclear leucocytes (PMN) that lyse in the crevice also contribute to the LDH pool. BG is said to be primarily derived from degradation of lysosomal granules of PMN with macrophates contributing to the BG pool. The pattern of AS activity was characterized as being between that of LDH and BG with sources of this enzyme including PMN, mast cells and fibroblasts.

Crevicular fluid "resting" volumes were determined by inserting a filter paper strip into the gingival sulcus until mild resistance was felt and leaving the strip in place for 30 seconds before determining the volume of fluid absorbed. After removal of the strip, the crevicular fluid "flow" volume was determined by waiting 30 seconds and inserting a second filter paper strip into the site for 3 seconds. Analysis of data collected from subjects subjected to experimental gingivitis indicated that while clinical inflammation increased during the 4 weeks of the study, the concentrations and total activity (concentration times sample volume) of BG and AS rose during the onset of gingivitis but peaked or leveled off after reaching a maximum 2 or 3 weeks into the study. The data indicated that an increase in fluid volume without a corresponding increase in BG or AS activity occurred during the latter part of the trial. The increase in LDH concentration and total activity during the experiment was not dramatic and was consistent with an earlier experiment wherein the concentration of LDH in crevicular fluid was higher in subjects with healthy gingiva than with mildly inflamed gingiva. Lamster, et al. also suggested that reporting of crevicular fluid constituent data in terms of concentration alone might be inadequate and that it might be desirable to report enzyme data in terms of both concentration and total activity of the sample.

Lamster, et al., J. Clin. Periodontol., 13, 799-804 (1986) present data wherein LDH, BG and AS concentrations and total activities for 30 second samples were assayed for a group of periodontitis patients and a control group. Negative or low positive correlation coefficients were determined between enzyme concentrations and gingival index (GI) and probing depth. On the other hand, "a modest, but not absolute" correlation between increasing severity of pathology and total enzyme activity for a 30 second sample was suggested by the data. Lamster, et al. suggested therefore that total activity in a standardized sample might be a more appropriate means of reporting crevicular fluid constituent data.

In spite of the various advances made in the art, the art still fails to provide a simple, reliable means for an enzymatic determination of the type and severity of periodontal disease. Such a method might be used for diagnosis of such disease or for determination of the efficacy of treatment of that periodontal disease condition. There currently exists no completely suitable means for determining the efficacy of treatment for periodontal disease. Such monitoring is a nontrivial concern because of the serious nature of continuing or repeating treatments for periodontitis involving administration of drugs, root planing or surgery. Current methods comprise monitoring of the clinical parameters of gingival bleeding, probing depths and radiographic interpretations of the bone. Because monitoring of probing depths and bone levels provides only a belated evaluation of treatment efficacy, an improved approach is clearly desired.

SUMMARY OF THE INVENTION

The present invention presents a method for determining the severity and type of periodontal disease states through assaying gingival crevicular fluid for the presence of elevated levels of AST. Specifically, the invention is based on the discovery that there exists a correlation between periodontal disease type and severity and the total activity of AST present in a sample of crevicular fluid taken for a selected brief period of time. It has been found that the total activity of AST present in a crevicular fluid sample taken for a selected brief period of time provides a better correlation with periodontal disease activity than does assaying for the AST concentration of crevicular fluid. It has been found that not only is the total activity of AST in crevicular fluid samples taken according to this method indicative of the severity of the disease state, but that it may be used contrary to the teachings of the art to distinguish between the disease states of gingivitis and periodontitis and thus identify the type of periodontal disease present.

Specifically, the invention provides a method for determining the severity and type of periodontal disease, the method including the steps of (1) sampling crevicular fluid for a selected brief period of time, (2) assaying the crevicular fluid sample so collected for the total quantity of AST present, and (3) correlating the total quantity of AST present in the crevicular fluid sample with a standard for the selected sampling period which is indicative of the presence and severity of periodontal disease. The invention also provides a method for determining the efficacy of treatment of periodontal disease conditions.

The method of the invention involves sampling of crevicular fluid according to a specific methodology whereby crevicular fluid at a given site is sampled over a selected brief period preferably of from about one second to about 3 minutes and most preferably from about 5 to 30 seconds. The crevicular fluid samples so obtained will be of varying volumes depending upon the condition of the specific sample site. The crevicular fluid so sampled, of whatever volume, is then assayed to determine, not the concentration, but the total activity of AST present. The activity of AST in the sample so assayed is then correlated with a standard established for the specific period of sampling time which standard is indicative of the severity and type (i.e., gingivitis or periodontitis) of periodontal disease. The improved methods of the invention are not only useful for the diagnosis of periodontal disease but are also useful for determining the efficacy of treatment of periodontal disease conditions by determining the severity of the periodontal disease condition at a gingival site subjected to such treatment.

DETAILED DESCRIPTION

According to practice of the invention, crevicular fluid is sampled from the intracrevicular space between the teeth and gum tissue for a selected brief period of time. The entire volume of fluid sampled during that time is then assayed to determine the total activity of AST present according to methods well known to the art. The quantity of AST determined is then correlated with a standard for the selected sampling period which is indicative of the severity and type of periodontal disease.

Crevicular fluid may be collected from the gingival sulcus by a variety of means according to the present invention including a microsyringe with a fine (preferably blunt) needle or a capillary tube which need not be calibrated. Samples may also be obtained by means of pledgets, cotton swabs or filamentous material such as dental floss. Preferably, such fluid is sampled by means of absorbant strips of paper such as those known as Periopaper (Harco; Tustin, Calif.). The sample is collected by direct contact of the sampling means with crevicular fluid at the gingival sulcus. The sample means should be of sufficient capacity to accommodate the volume of crevicular fluid collected for the selected sampling period. It is generally desirable that this volume should be less than or equal to about 1 $\mu$l but the sample volume could be substantially higher (i.e., from 1–10 $\mu$l) when the flow rate is greatly elevated. It is not generally necessary for sample volumes to exceed 1 $\mu$l, however, as AST levels of samples exceeding such volumes typically contain sufficient AST as to be indicative of severe periodontitis for selected sampling periods. The fluid sampled can be less than the total capacity of the sample means. The absence of enzyme or of fluid at a crevicular site is generally indicative of health and may be interpreted as such. It is not necessary that the absorbant means measure the volume of the fluid absorbed but it is generally desired that the means absorb all of the fluid in the crevicular space, for a given time period.

The method of the invention involves sampling of crevicular fluid according to a specific methodology whereby crevicular fluid at a given site is sampled over a selected brief period preferably of from about 5 seconds to about 3 minutes and most preferably from about 5 to 30 seconds. The oral fluid sample, obtained by whatever means, is then assayed to determine the quantity of AST present. Chemical or immunological methods such as are well known in the art may be used to conduct such analysis. Such methods are disclosed in detail in Chambers, European Patent Application No. 151,536 and its corresponding U.S. application, the disclosure of which is hereby incorporated by reference, and utilize the AST catalyzed reaction of substrates to produce a detectable reaction product. The Chambers, European Patent Application also discloses immunological assays for the determination of AST concentrations. A particularly preferred enzymatic method is that disclosed in U.S. Pat. No. 4,801,535, the disclosure of which is hereby incorporated by reference. Methods according to PCT/US87/00541 are directed to the determination of the presence of sub- and suprathreshold concentrations of AST and may be particularly useful according to the present invention for evaluating test samples and distinguishing between those samples indicative of periodontitis samples indicative of gingivitis and samples indicative of absence of active disease, i.e., absence of periodontitis and absence of gingivitis.

EXAMPLE 1

In this example a study of experimental gingivitis and periodontitis in beagle dogs was conducted according to the methods described in the Crawford, et al. and Mukherjee, et al. Abstracts, the Chambers, et al. J. Periodontol. (1984) publication and Chambers, European Patent Application No. 151,536 recited above.

Six beagle dogs were fed on a hard diet and given daily oral hygiene for one month in order to establish a state of gingival health. Before and after the month of oral hygiene and hard diet, AST activity was measured in gingival crevicular fluid (GCF) specimens collected from buccal sites around the 12 premolar teeth of each dog. Clinical measurements of periodontal status were also made. After one month of oral hygiene, the dogs were put on a soft diet and daily oral hygiene ceased, in order to induce gingivitis. After 6 weeks of soft diet and no daily oral hygiene, ligatures were placed on 6 premolar teeth of each dog; the other 6 premolar teeth of each dog served as matched controls. Therefore in each individual dog, there were 6 ligated teeth which were induced to develop attachment loss and also 6 control teeth which did not develop attachment loss.

In this study, GCF specimens were collected by means of Periopaper strips (Harco, Tustin, Calif.) which were inserted into the crevicular space between the gum and tooth. The Periopaper strip was held in place for the period of time required to collect samples ranging in volume from 0.2 $\mu l$ to 1.0 $\mu l$. In this study, the collection period ranged from 1 second to 10 minutes. The fluid volume of each GCF specimen was then measured by means of a Periotron digital fluid meter (Harco Electronic Devices, Inc., Irvine, Calif.). The crevicular fluid flow rate for each site was then calculated from the volume and the time period of specimen collection. AST activity was measured by means of a standard spectrophotometric method for quantitative kinetic determination of AST activity. In order to compare AST activity of samples of various different volumes and collected for various different collection periods, the AST activity for each GCF specimen was then calculated by two different methods: (1) as the concentration of AST activity per unit volume, based on the AST activity in the GCF specimen and the specimen volume; and (2) as the total AST activity per 30 seconds, based on the AST activity in the GCF specimen and the flow rate. It was found that a closer correlation could be demonstrated between disease activity and AST activity calculated as total AST activity in 30 seconds, than between disease activity and AST activity calculated as concentration of AST activity per volume.

The study of ligature-induced periodontitis demonstrated a positive association between loss of attachment and elevated AST activity at ligated sites. Attachment loss of 2 or more mm (ALOSS) occurred at 68/92 (73.9%) of the ligated sites. The ALOSS interval (during which significant changes in attachment level occurred) was determined for each of these sites. The number of ALOSS sites, which had one or more elevated AST measurements coinciding with the ALOSS interval for that site, were then tabulated (Table 1). The number of nonligated control sites (matched with each ligated ALOSS site) which had elevated AST measurements were also tabulated for comparison. Each row of the table lists the cumulative number of sites associated with AST measurements above each of the cutoff levels indicated. The cutoff level defines elevated AST, and determines how sensitive AST levels are in distinguishing between ALOSS and control sites. AST levels were determined by two different methods—as concentration of AST activity per unit volume of crevicular fluid and as total AST activity per 30 seconds (see above). Table 1 indicates that when AST activity was determined as concentration, there was little distinction between ALOSS sites and matched controls at all of the cutoff levels. The cumulative number of ALOSS sites with AST concentrations above the cutoff did not differ much from the cumulative number of control sites at each cutoff level: there were only 5 ALOSS sites with AST concentrations above 3000 $\mu IU/\mu l$, compared to 2 control sites with AST concentrations above 3000 $\mu IU/\mu l$; there were only a total of 10 ALOSS sites with AST concentrations above 2000 $\mu IU/\mu l$, compared to 8 control sites. When AST activity was calculated as total activity obtainable in 30 seconds, there was a clear distinction between ALOSS sites and controls at all cutoff levels. Furthermore, in nearly all of the ALOSS sites, the peak levels of AST activity (total AST/30 sec.) were temporally associated with loss of attachment level.

TABLE 1

Study of Ligature-Induced Periodontitis Number of Sites with Elevated AST During Attachment Loss (ALOSS)

| AST* Cutoff ($\mu IU/\mu l$) | AST Concentration | | AST* Cutoff ($\mu IU$) | Total AST Activity/30 Sec. | |
|---|---|---|---|---|---|
| | ALOSS | Control | | ALOSS | Control |
| 3000 | 5 | 2 | 3000 | 39 | 0 |
| 2000 | 10 | 8 | 2000 | 49 | 0 |
| 1500 | 16 | 12 | 1500 | 55 | 0 |
| 1200 | 18 | 18 | 1200 | 59 | 0 |
| 800 | 31 | 34 | 800 | 65 | 0 |
| 500 | 44 | 55 | 500 | 65 | 3 |
| Total | 68 | 68 | | 68 | 68 |

*Each "cutoff" level defines elevated AST, i.e., there were 5 ALOSS sites with AST concentrations greater than 3000 $\mu IU/\mu l$, and 2 control sites with AST concentrations greater than 3000 $\mu IU/\mu l$. At 2000 cutoff, there were a total of 10 sites with AST concentrations greater than 2000 $\mu IU/\mu l$ and 8 control sites with AST concentrations greater than 2000 $\mu IU/\mu l$.

In addition to providing evidence to associate elevated AST activity and attachment loss, the study also demonstrated a positive association between gingival inflammation and elevated AST activity in gingival crevicular fluid of ligated sites. Although significant attachment loss did not occur at 24 of the 92 ligated sites, the incidence of marked gingival inflammation at all of these sites was indicative of periodontal disease activity. In addition, in most of the 68 ligated sites which did exhibit significant attachment loss, there was a high incidence of gingival inflammation after attachment loss as well as during attachment loss. Although the period of attachment loss for 59 of the 68 attachment loss sites was during the first 1½ weeks after placement of the ligatures, the incidence of gingival inflammation during the last 2 weeks of ligation was indicative of further disease activity beyond the attachment loss interval. (Attachment loss during the last 2 weeks of ligation occurred at only 9 of the 68 attachment loss sites). At 66% of the ligated sites, there was obvious inflammation (indicated by Gingival Index $\geq 2$) that was not coincident with attachment loss; only 8% of the nonligated control sites exhibited this level of inflammation during the same period. Therefore, the finding that inflammation was much more frequent at ligated sites suggested that the inflammation was associated with destructive disease processes. Table 2 shows how often this inflammation was associated with elevated levels of AST activity. When the AST activity was calculated as total activity per 30 second sample, most of the inflamed sites also had elevated levels. When the AST activity was calculated as concentration per unit volume, however, this association was less apparent, since few ligated sites had AST levels that were higher than nonligated control sites. These results demonstrated a positive association between elevated AST activity expressed as total activity per 30 seconds and gingival inflammation associated with disease activity.

TABLE 2

Dog Study of Ligature-Induced Periodontitis
Number of Sites with Elevated
AST Coincident with Inflammation (Gingival Index ≧ 2)

| AST Cutoff (μIU/μl) | AST Concentration | | AST Cutoff (μIU) | Total AST Activity/30 Sec. | |
|---|---|---|---|---|---|
| | ALOSS | Control | | ALOSS | Control |
| 3000 | 3 | 0 | 3000 | 31 | 0 |
| 2000 | 8 | 1 | 2000 | 36 | 0 |
| 1500 | 13 | 5 | 1500 | 41 | 1 |
| 1200 | 22 | 10 | 1200 | 45 | 2 |
| 800 | 34 | 35 | 800 | 46 | 2 |
| 500 | 42 | 48 | 500 | 46 | 2 |
| Total | 49 | 49 | | 49 | 49 |

When AST levels are measured in terms of total activity in a 30 second sample as opposed to concentration of enzyme activity per volume, the relationship between AST and the severity and type of periodontal disease state is more readily apparent. (See Table 3.) While AST concentration distinguishes between ligated and non-ligated teeth, there is little apparent difference between AST concentrations when compared between the baseline, health and gingivitis states. In contrast, comparison of AST quantity in calculated 30 second samples provides clear distinctions between ligated (experimental periodontitis) teeth and teeth during the health, baseline and gingivitis states.

This example demonstrates that elevated total quantities of AST in timed crevicular fluid samples are closely associated with the occurrence of attachment loss. Furthermore, the example also demonstrates that during the period of ligature-induced disease activity, elevated AST activity was also associated with high frequencies of gingival inflammation.

TABLE 3

| | AST Conc. μIU/μl | Calculated 30 Sec. Sample AST Content μIU |
|---|---|---|
| Baseline (n = 182) | 954.9 ± 609.3 | 65.7 ± 77.8 |
| Health (n = 171) | 610.4 ± 224.9 | 15.0 ± 7.3 |
| Gingivitis (n = 175) | 656.2 ± 380.4 | 43.0 ± 53.5 |
| Non-Ligated Teeth | 661.1 ± 138.3[a] | 58.1 ± 36.6[b] |
| Ligated Teeth | 1207.4 ± 419.5[a] | 6502.0 ± 4765.2[b] |

[a] t = 8.451, p < 0.001
[b] t = 8.056, p < 0.001
t statistic resulting from a paired t-test in which the mean AST for each of 36 ligated teeth was paired with the mean AST of the contralateral non-ligated tooth.

EXAMPLE 2

In this example, a longitudinal study of periodontitis was conducted of 34 human subjects moderately at risk for periodontitis but not receiving treatment. Up to fifty-two (52) sites per subject were evaluated clinically and assayed for the presence of AST on a quarterly basis for from three to seven quarters. Each of the sites on each of the patients were assayed for AST activity according to the procedure of Example 1 by inserting a strip of Periopaper (Harco; Tustin, Calif.) into the gingival crevicular space and sampling crevicular fluid for varying time periods with the sampling period recorded for each sample. The AST concentrations of the crevicular fluid samples so obtained were then determined by conventional assay methods. While specific limited volumes of crevicular fluid were sampled the crevicular fluid flow rates could be calculated on the basis of the time required to draw the samples. It was then possible to determine the amount of AST that would have been present if the samples had been taken for a 30 second period of time.

Figure 1A:
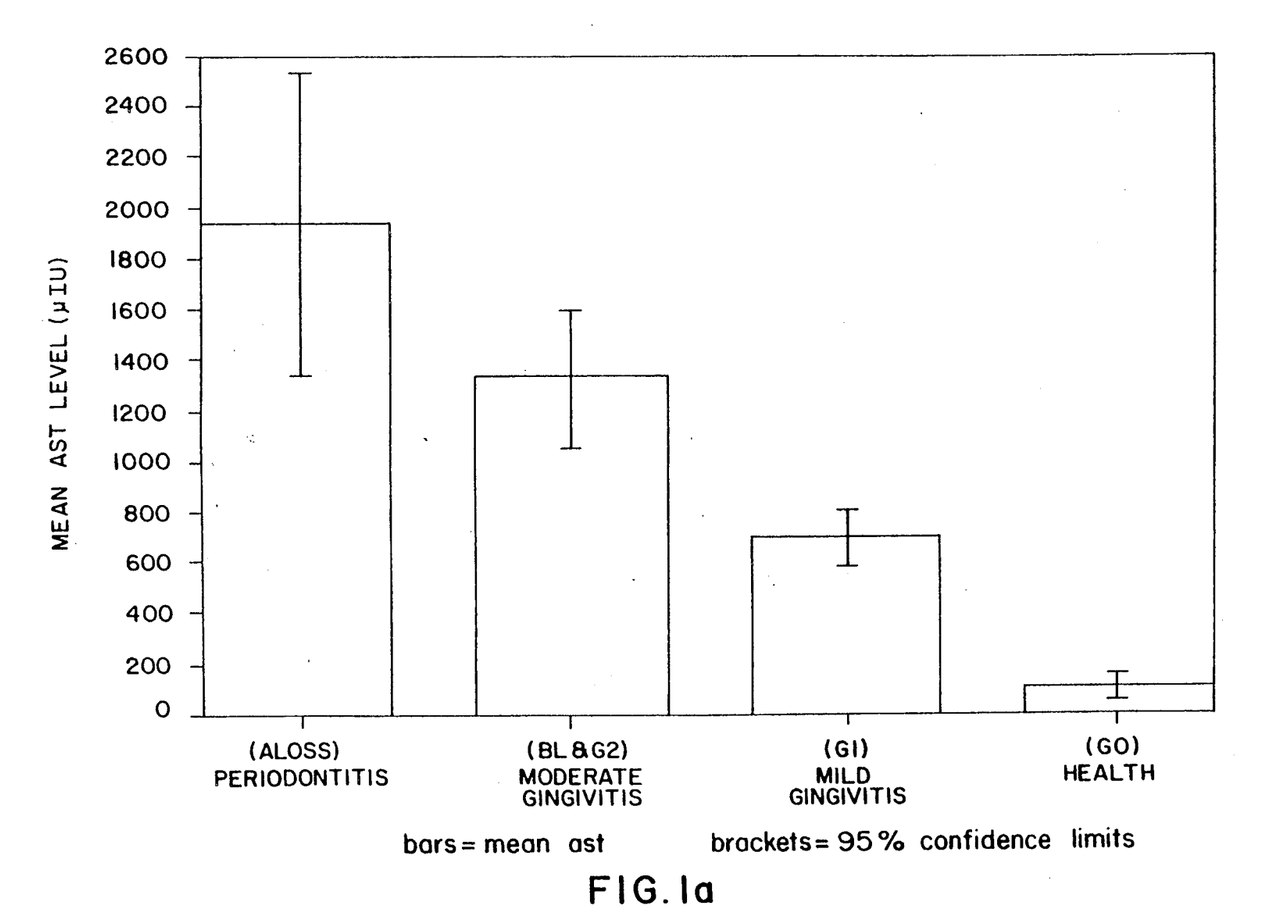
FIG. 1a illustrates the relationship between total AST enzyme levels in timed samples and periodontal disease severity and type.
Figure 1B:
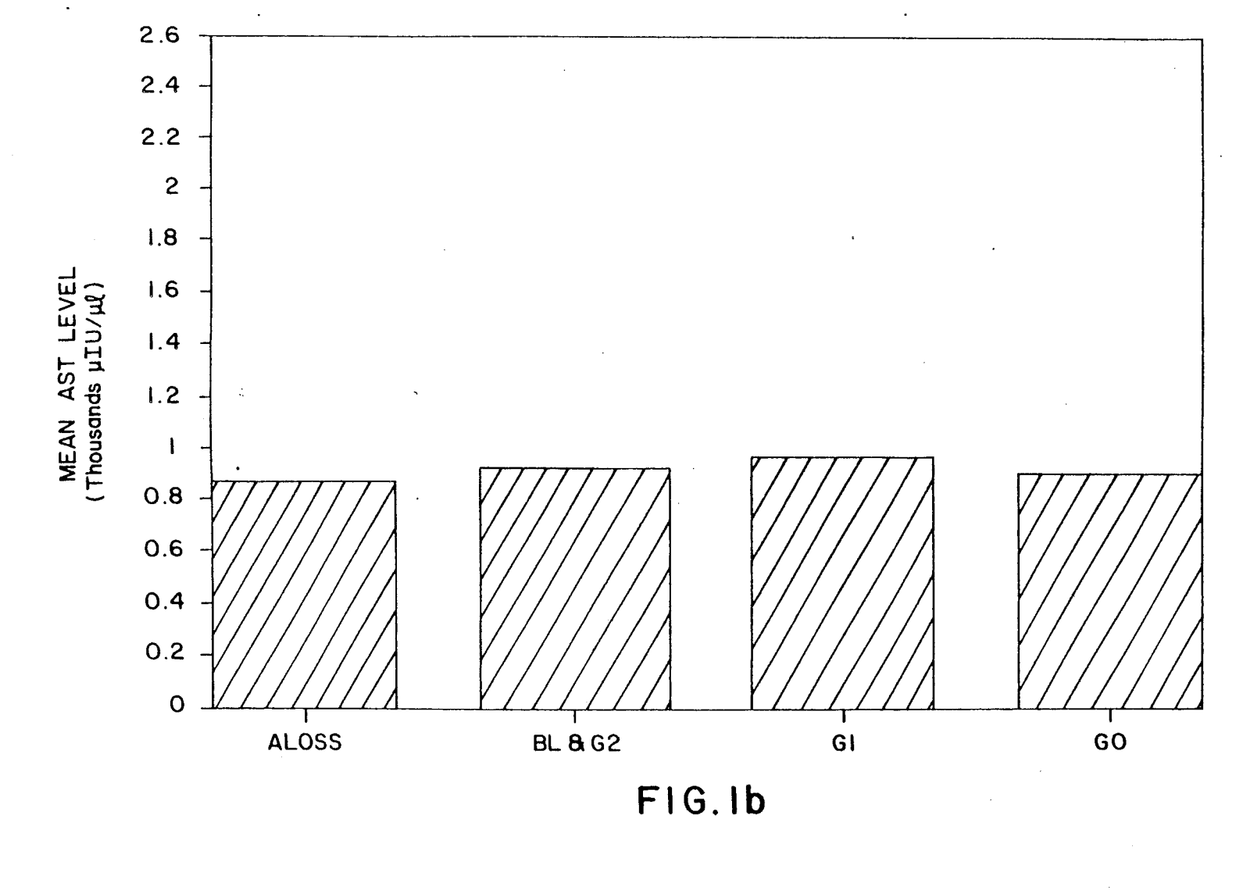
FIG. 1b illustrates the relationship between AST enzyme concentration and periodontal disease severity and type.

Crevicular fluid specimens were collected from up to 52 sites per subject once every 3 months for 6–18 months. Clinical measurements of periodontal status including pocket depth, attachment level, Gingival Index and bleeding upon probing, were also made each quarter. The clinical measurements were used to determine the severity of disease activity occurring at each gingival site. In order to evaluate the association between AST activity and disease severity, all of the study sites were assigned to 1 of 4 different categories of disease activity (Table 4). The mean AST activity for each site was calculated and then the mean AST of all of the sites within each category was determined. When AST per 30 second sample was used to calculate the mean AST activity levels for the 4 categories of disease activity, there was an obvious correlation between the magnitude of AST activity and disease severity (see FIG. 1a wherein the bars indicate the means AST level and the brackets about each bar indicate the 95% confidence limits indicated by the collected data.) The highest mean AST levels were associated with the most severe disease activity—i.e., loss of attachment. The level of AST activity also correlated with the degree of gingival inflammation and bleeding, i.e., higher mean AST levels were associated with mode Gingival Index=2 and/or frequent bleeding upon probing; lower levels were associated with mild gingivitis, mode Gingival Index=1; and the lowest levels were associated with gingival health, mode Gingival Index=0 (FIG. 1a). In contrast, when AST concentration was used, there was no significant distinction between the different categories of disease severity (FIG. 1b). These findings were consistent with those of Example 1 in which AST activity calculated as total activity per 30 seconds correlated much better with disease activity than concentration of AST activity. Furthermore, elevated AST was correlated with degree of gingivitis as well as periodontitis.

TABLE 4

Hierarchy of Periodontal Disease Activity

| Category | Definition |
|---|---|
| Periodontitis ALOSS Attachment Loss | Confirmed attachment loss (ALOSS) of ≧ 2 mm during the study. Confirmed ALOSS is ≧ 2 mm deepening of probing attachment level which was confirmed by subsequent attachment level measurment(s). |
| Gingivitis | |
| G2 Moderate Gingivitis | Sites which did not exhibit confirmed ALOSS and which had mode[a] Gingival Index = 2 OR bled upon gently probing most of the quarters studied. |
| G1 Mild Gingivitis | Sites which did not exhibit confirmed ALOSS and which had mode Gingival Index = 1. |
| G0 Health | Sites which did not exhibit confirmed ALOSS and which had mode Gingival Index = 0. |

[a] Mode GI = most frequent Gingival Index; when 2 GI were equally frequent, the higher GI was used.

Analysis of the data generated indicated a clear distinction between most sever disease activity, as represented by attachment loss (ALOSS), and least severe disease activity (GO) when AST activity was calculated as total AST activity for a 30 second sample. There was little distinction between diseased and healthy sites, however, when AST activity was calculated as concentration. (See Table 5.)

TABLE 5

CUMULATIVE NUMBER OF SITES WITH MAXIMAL AST LEVEL/SITE DURING ATTACHMENT LOSS (OR ANY VISIT FOR HEALTHY SITES)

| Ast CUTOFF LEVEL ($\mu$IU) | TOTAL AST/30 SEC | | AST CUTOFF CONC. ($\mu$IU/$\mu$l) | AST CONCENTRATION | |
|---|---|---|---|---|---|
| | ALOSS | HEALTH* | | ALOSS | HEALTH |
| >2000 | 29 | 4 | >2000 | 7 | 3 |
| >1500 | 34 | 8 | >1500 | 16 | 11 |
| >1000 | 36 | 9 | >1000 | 31 | 42 |
| >900 | 36 | 11 | >900 | 36 | 59 |
| >800 | 38 | 12 | >800 | 40 | 71 |
| >700 | 40 | 12 | >700 | 40 | 88 |
| >600 | 40 | 13 | >600 | 43 | 92 |
| >500 | 40 | 16 | >500 | 46 | 104 |
| Total | 49 | 131 | Total | 49 | 131 |

*Healthy sites were those sites with no significant change in attachment level and mode Gingival Index = 0 (see Table 4).

The distinction between presence of disease (ALOSS) and no disease was also demonstrated by a rank randomization argument which compared diseased sites and healthy sites within each subject individually.

Figure 2:
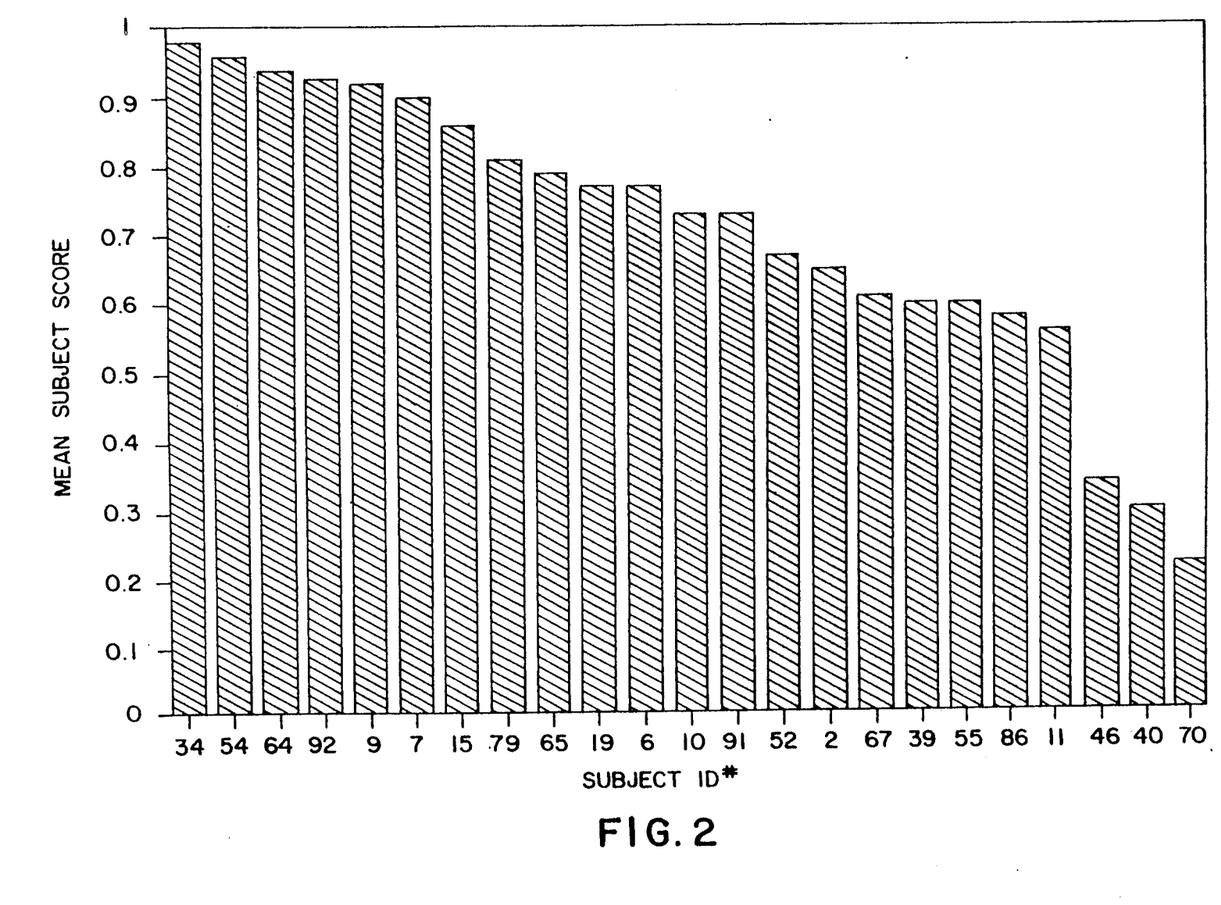
FIG. 2 illustrates a statistical relationship between elevated AST enzyme levels and attachment loss.

When the data for calculated 30 second AST samples was analyzed by this rank randomization argument, AST was shown to have a highly significant association with the occurrence of attachment loss. (See FIG. 2.) If there was no association between elevated AST levels and attachment loss, the summary index for that patient would be less than or equal to 0.5 while if there was a positive association between elevated AST and attachment loss, the summary index would be greater than 0.5. Of the twenty-three (23) patients with one or more attachment loss sites, (58 sites total) twenty (20) had an index greater than 0.5, a highly significant result. (p=0.000244) The control consisted of 597 sites distributed among 23 subjects judged healthy. The study therefore not only indicated an association between elevated levels of AST and periodontal disease, but also indicated a strong association (as well as a temporal relationship) between AST and periodontitis.

EXAMPLE 3

A second study similar to that of Example 2 was conducted wherein all crevicular fluid samples were taken by sampling crevicular fluid with periopaper strips for 30 seconds from eight (8) gingival sites in each of twenty-five (25) human subjects with histories of periodontitis. AST assays and clinical assessments were made quarter annually for from three to seven quarters.

Figure 3:
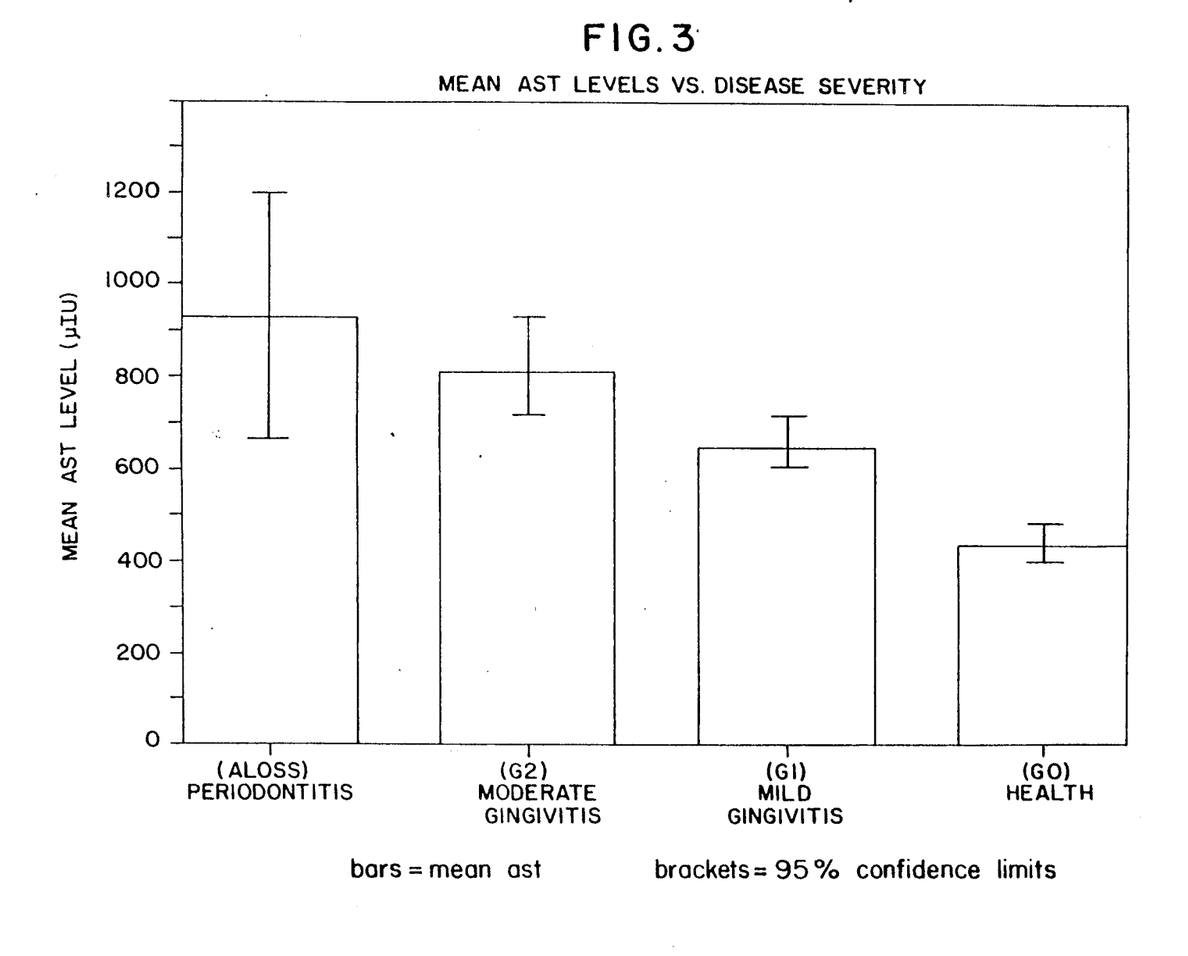
FIG. 3 illustrates the relationship between total AST enzyme levels in timed samples and periodontal disease severity and type.

In this study, each crevicular fluid specimen was collected for a uniform sampling time period of 30 seconds and AST activity was calculated only as total activity per sample. Clinical measurements of periodontal status such as pocket depth, attachment level and Gingival Index, were also made each quarter. As in the study of Example 2, the clinical measurements were used to determine the severity of disease activity occurring at each gingival site. The sites were assigned to categories of disease severity and mean AST levels per site were used to plot FIG. 3 wherein the bars indicate the mean AST level and the brackets about each bar indicate the 95% confidence limits indicated by the collected data. This graph shows a correlation between magnitude of AST activity and severity of periodontal disease that is similar to FIG. 1.

Thus, the results of two separate studies of naturally occurring periodontal disease in humans confirmed that the highest level of AST activity in gingival crevicular fluid were associated with significant attachment loss (periodontitis). Furthermore, both studies demonstrated that elevated AST levels were also associated with moderate gingivitis; lower levels were associated with mild gingivitis, and the lowest levels were associated with no gingivitis.

The human study of this example was carried out on subjects enrolled in a maintenance program, which provided quarterly root planning and scaling. Although some sites exhibited significant loss of attachment despite this regular therapy, some sites exhibited significant gain in attachment which could be attributed to successful therapy. Thirty-one study sites distributed among 15 of the subjects exhibited significant gain of attachment, classified as a gain in attachment of greater than or equal to 2 mm. For 23 of these sites (74%), the gain in attachment level was associated with a drop in the level of AST activity; whereas in only 9 of these sites (26%), was the gain associated with a rise in AST activity. Furthermore, the mean drop in AST associated with gain of attachment (mean drop=492 $\mu$IU) was more than twice as great as the mean rise in AST (mean rise=210 $\mu$IU). Therefore, in 72% of the cases in which maintenance therapy was effective, there was a drop in AST coincident with the gain of attachment. When the data was analyzed by the Wilcoxon Signed Ranks Test, the drop in AST levels associated with gain of attachment was found to be highly significant, p=0.002. These results indicated that decreasing AST activity often coincided with decreasing disease activity. Therefore, measurement of AST activity in GCF would be useful not only as a diagnostic tool for detecting the occurrence of disease, but it would also be useful for monitoring responsiveness to therapy.

Numerous modifications and variations of the above-described invention are expected to occur to those of skill in the art. In particular, it is expected that modifications of the assay procedures will be developed for colorimetric assay kits indicative of the potential presence and severity of any periodontal disease state. Accordingly, only such limitations as appear in the appended claims should be placed thereon.

What is claimed is:

1. A method for determining the severity and type of periodontal disease in mammals comprising the steps of
   (1) sampling crevicular fluid for a selected brief period of time,
   (2) assaying the crevicular fluid sample so collected to determine the total quantity of aspartate aminotransferase present, and
   (3) correlating the total quantity of aspartate aminotransferase present in said crevicular fluid sample with a standard for the selected period of time indicative of the severity and type of periodontal disease.

2. A method determining the efficacy of treatment of periodontal disease conditions, said method comprising the steps of
   (1) sampling crevicular fluid for a selected brief period of time,
   (2) assaying the crevicular fluid sample so collected for the total quantity of aspartate aminotransferase present, and
   (3) correlating the total quantity of aspartate aminotransferase present in said crevicular fluid sample with a standard for the selected period of time indicative of the degree of severity and type of the periodontal disease state.

3. The method according to claims 1 or 2 wherein crevicular fluid is sampled for between 1 second and 3 minutes.

4. The method according to claim 3 wherein crevicular fluid is sampled for between 5 seconds and 30 seconds.

5. The method according to claims 1 or 2 wherein crevicular fluid is sampled by means of an absorbant tip.

6. The method according to claims 1 or 2 wherein said assay is a colorimetric assay.

7. The method according to claim 6 wherein said assay is a semi-quantitative assay which indicates the presence of a selected suprathreshold quantity of aspartate aminotransferase.

* * * * *

UNITED STATES PATENT AND TRADEMARK OFFICE
CERTIFICATE OF CORRECTION

PATENT NO. : 5,047,328

DATED : September 10, 1991

INVENTOR(S) : Chambers et al.

It is certified that error appears in the above-identified patent and that said Letters Patent is hereby corrected as shown below:

Abstract, lines 7-8, "aspara-tate" should be --aspartate--.

Column 10, line 67, "higher" should be underlined.

Column 11, line 2, "sever" should be --severe--.

Column 11, line 4, "(GO)" should be --(GO)--.

Column 11, Table 5, line 14, first column "Ast" should be --AST--.

Column 10, line 50, "Periodontitis" and line 59, "OR" should be underlined.

Signed and Sealed this

Twentieth Day of July, 1993

Attest:

MICHAEL K. KIRK

Attesting Officer    Acting Commissioner of Patents and Trademarks